US006013264A

United States Patent [19]
Petre et al.

[11] Patent Number: 6,013,264
[45] Date of Patent: Jan. 11, 2000

[54] VACCINE

[75] Inventors: Jean Petre; Pierre Hauser, both of Belgium, Belgium

[73] Assignee: Smithkline Beecham Biologicals, Rixensart, Belgium

[21] Appl. No.: 08/755,927

[22] Filed: Nov. 25, 1996

Related U.S. Application Data

[63] Continuation of application No. 08/400,313, Mar. 6, 1995, abandoned, which is a continuation of application No. 08/065,315, May 21, 1993, abandoned.

[30] Foreign Application Priority Data

May 23, 1992 [GB] United Kingdom .............. 9211081
Jun. 23, 1992 [GB] United Kingdom .............. 9213308

[51] Int. Cl.$^7$ ............... A61K 39/29; A61K 45/00; A61K 39/13; A61K 39/295
[52] U.S. Cl. ........................ 424/227.1; 424/226.1; 424/184.1; 424/278.1; 424/189.1; 424/203.1; 424/201.1; 424/217.1; 424/450; 424/202.1
[58] Field of Search ............... 424/184.1, 278.1, 424/227.1, 189.1, 203.1, 201.1, 202.1, 226.1, 217.1

[56] References Cited

U.S. PATENT DOCUMENTS 5,151,023  9/1992  Kuzuhara et al. ............ 424/89
5,776,468  7/1998  Hauser et al. .

FOREIGN PATENT DOCUMENTS 130 619      1/1985   European Pat. Off. .
156 242     10/1985   European Pat. Off. .
0 339 667    2/1989   European Pat. Off. ....... A61K 39/69
339 667     11/1989   European Pat. Off. .
533 492      3/1993   European Pat. Off. .
WO 92/11291  7/1992   WIPO .

OTHER PUBLICATIONS

Research Disclosure (1991) Sep., 32975 –Polyvalent Antigen Vaccine for Human Use.
Sigma Catalogue (1990) –pp. 147–148.
Sigma Catalogue (1998) –pp. 89–90.
Brummelhuis H G J et al (1981) —Hepatitis B Vaccine –INSERM Symposium No 18 –pp. 51–56.
Lafeber–Schut LJ Th (1981) —Hepatitis B Vaccine –INSERM Symposium No 18 –pp. 105–113.
Coutinho R A et al. (1983) —Develop. Biol. Standard 54:287–292.
Mazert M–C et al (1983) —Develop. Biol. Standard 54:53–62.
Coursaget P et al (1986) —Develop. Biol. Standard 65:169–175.
Coursaget P et al (1986) —Infection and Immunity 51:784–787.
Yvonnet B et al (1986) —Develop. Biol. Standard 65:205–207.
Van Damme P et al (1994) —Viral Hepatitis & Liver Disease –pp. 514–516.
Plotkin S A & Mortimer E A (Eds) (1988) —Vaccines W B Saunders Company –p. 55.
Physicias Desk Reference (1994) —pp. 1149–1151.
Chiron, et al., "Simultaneous Administration of Hepatitis B and Diphtheria/Tetanus/Polio Vaccines", (1984), *Lancet*, 1:623–624.
F. Andre, et al., "Global Perspectives on Hepatitis", (1983), *Perspectives*, vol. 4, No. 1, pp. 1–8.
"Polyvalent antigen vaccine for human use", (1991), *Research Disclosure*, 329.
Coursaget, et al., "Simultaneous Administration of Diphtheria–Tetanus–Pertussis–Polio and Hepatitis B Vaccines in a Simplified Immunization Program: Immune Response to Diphtheria Toxoid, Tetanus Toxoid, Pertussis, and Hepatitis B Surface Antigen" (1986), *Infection and Immunity*, vol. 51, No. 3, pp. 784–787.
Murphy, et al., "Evaluation of the Pertussis Components of Diphtheria–Tetanus–Pertussis Vaccine", (1983), *Pediatrics*, vol. 71, No. 2, pp. 200–205.
Giammanco, et al., "Immune response to simultaneous administration of a recombinant DNA hepatitis B vaccine and multiple compulsory vaccines in infancy", (1991), *Vaccine*, 9:747–750.
Goto, et al., "Accumulation of Ascites and Increase in Skin Vascular Permeability Observed by Injection of Adsorbed Diphtheria–Purified Pertussis–Tetanus Combined Vaccine in Guinea Pigs", (1991), *Microbiol. Immunol.*, vol. 35, (12), pp. 1143–1148.
Coursaget, et al., "Simultaneous Administration of Diphtheria–Tetanus–Pertussis–Polio Vaccine and Hepatitis B Vaccine in a Simplified Immunization Programme" (1985), *Develop. biol. Standard.*, vol. 65, pp. 169–175.
N. Letvin, "Vaccines Against Human Immunodeficiency Virus —Progress and Prospects", (1993), *The New England Journal of Medicine*, 329(19):1400–1405.
Polyvalent Antigen Vaccine for Human Use Research Disclosure 329, 1991.

*Primary Examiner*—Nita Minnifield
*Attorney, Agent, or Firm*—Zoltan Kerekes; Stephen Venetianer; Charles M. Kinzig

[57]          ABSTRACT

Stable and effective multivalent vaccine compositions comprising Hepatitis B surface antigen (HBsAg) are described wherein the HBsAg component is stable for one week at 37° C. and is highly immunogenic, for example when the vaccine is administered to infants. The compositions typically comprise HBsAg adsorbed to aluminium phosphate and other antigens, especially those suitable for use in a paediatric vaccine, adsorbed to aluminium phosphate or aluminium hydroxide. Methods for preparing the vaccines and the use of aluminium phosphate to stabilise HBsAg in a multivalent vaccine formulation are also described.

20 Claims, No Drawings

VACCINE

This is a continuation of application Ser. No. 08/400,313, filed Mar. 6, 1995, now abandoned, which is a continuation of application Ser. No. 08/065,315, filed May 21, 1993, now abandoned, which claims priority from foreign applications GB 9211081.6, filed May 23, 1992 and GB 9213308.1, filed Jun. 23, 1992.

The present invention relates to novel vaccine formulations, methods for preparing them and to their use in therapy. In particular the present invention relates to novel combination vaccine formulations including a Hepatitis B vaccine component for treating Hepatitis B infections.

Infection with Hepatitis B (HB) virus is a widespread problem but vaccines which have been used for mass immunization are now available, for example the product 'Engerix-B'™ (SmithKline Beecham plc). Engerix B® has as the Hepatitis B antigenic component Hepatitis B surface antigen (HBsAg) which is obtained by genetic engineering techniques.

However, it is often necessary or desirable to administer Hepatitis B vaccine at the same time as other vaccines and this can involve multiple injections. Problems associated with multiple injections include a more complicated administration procedure and a large total injection volume.

There is therefore a need for a combined vaccine comprising a Hepatitis B antigen in combination with other antigens. The other antigens are in particular those capable in a vaccine formulation of preventing Hepatitis A (HA), diphtheria (D), tetanus (T), pertussis (P) [e.g., whole cell pertussis (Pw) or acellular pertussis (Pa)], Haemophilus influenzae b (Hib) and polio (P).

Aluminium hydroxide (AH) is widely used as an adjuvant in the formulation of vaccines. For example, Engerix B™® uses Hepatitis B surface antigen (HBsAg) adsorbed to aluminium hydroxide. AH has also been used in the formulation of a Hepatitis A vaccine and in combination vaccines: DT, DTPw and DTPa. However, when AH-adsorbed HBsAg is used in combination with other vaccines, there is a substantial decrease of the immune response to HBsAg resulting in lower or insufficient seroprotection after vaccination. In addition, the stability of the HBsAg component of the combined vaccine is poor.

Aluminium phosphate (AP) adsorbed HBsAg has been used in a commercially available monovalent vaccine (HEPPACINE)™ made by Korean Cheil Sugar Co Ltd.

European patent application publication number 0 339 667 discloses a bivalent vaccine comprising HBsAg and a Hepatitis A antigen in which either aluminium hydroxide or aluminium phosphate is used as adjuvant. There appears, however, to be no appreciation of the need to avoid aluminium hydroxide as an adjuvant for a multivalent vaccine comprising HBsAg. Furthermore, there appears to be no disclosure of a bivalent or multivalent hepatitis B vaccine in which at least one antigen other than HBsAg is adsorbed on aluminium hydroxide and the HBsAg is adsorbed on aluminium phosphate.

Indeed, there appears to be no prior enabling disclosure of a stable and effective multivalent vaccine comprising HBsAg.

In one aspect the present invention provides a combined vaccine composition comprising Hepatitis B surface antigen (HBsAg) and a number (n) of other antigens in combination with an adjuvant comprising one or more aluminium salts in which the value of n is 1 or greater and in which the adjuvant used to adsorb the HBsAg is not aluminium hydroxide, with the proviso that when n is 1 the other antigen is not an antigen against Hepatitis A. In calculating the number (n) for other antigens, n is considered to be one per pathogen. For example, an acellular pertussis vaccine which may comprise pertussis toxoid, filamentous hemagglutinin and the 69KDa outer membrane protein, is considered one pe-tussis antigen (i.e., n=1).

Preferably n is 1–10. More preferably, n is 2, 3, 4, 5 or 6.

One advantage of the invention is that no substantial decrease in the immunogenicity of the HBsAg occurs in the combined vaccine formulation. Avoiding the use of AH to adsorb the HBsAg component in the vaccine formulation also gives rise to a product of markedly superior stability. Another advantage of the invention is that the aforesaid problems associated with multiple injections are overcome or at least mitigated and a stable, highly immunogenic combined formulation is provided. The compositions of the invention are particularly suitable for administration to children.

Preferably the HBsAg is adsorbed on AP. In particular, we have found in human clinical studies that when AP-adsorbed HBsAg is combined with one or more AH-adsorbed or AP-adsorbed antigens in a combined vaccine, no substantial decrease in immunogenicity occurs. The stability of the AP-adsorbed HBsAg in the formulation is also greater than AH-adsorbed HBsAg.

Accordingly in a further aspect there is provided a vaccine composition according to the invention in which at least one of the antigens other than HBsAg is adsorbed to aluminium phosphate.

In a further preferred aspect at least one of the antigens other than HBsAg is adsorbed to AH.

In yet another aspect, the invention provides a combined vaccine comprising Hepatitis B surface antigen (HBsAg) adsorbed to AP and an antigen adsorbed to AP or to AH selected from an antigen providing immunity against one or more of the following pathogens: diphtheria (D); tetanus (T); pertussis (P); Inactivated Polio (IPV); Haemophilus influenzae b (Hib); and Hepatitis A (HA).

In a pediatric vaccine other compatible antigens may also be included, e.g., antigens known to be effective against meningitis B, meningitis A and C, and otitis media As used herein the term 'bivalent' is used to refer to a vaccine comprising a combination of two antigens in total (including HBsAg). The term 'multivalent' is applied to a vaccine composition comprising more than two antigens, for example, three, four or five or six antigens (i.e., $n \geq 3$).

The meaning of the terms 'aluminium phosphate' and 'aluminium hydroxide' as used herein includes all forms of aluminium hydroxide or aluminium phosphate which are suitable for adjuvanting vaccines.

For example, aluminium phosphate can be a precipitate of insoluble aluminium phosphate (amorphous, semi-crystalline or crystalline), which can be optionally but not exclusively prepared by mixing soluble aluminium salts and phosphoric acid salts. "Aluminium hydroxide" can be a precipitate of insoluble (amorphous, semi-crystalline or crystalline) aluminium hydroxide, which can be optionally but not exclusively prepared by neutralizing a solution of aluminium salts. Particularly suitable are the various forms of aluminium hydroxide and aluminium phosphate gels available from commercial sources for example, Alhydrogel™ (aluminium hydroxide, 3% suspension in water) and Adju-fos™ (aluminium phosphate, 2% suspension in saline) supplied by Superfos (Vedbaek, 2950 Denmark).

It will be appreciated that for the first time we are able to provide a stable and effective multivalent vaccine composition comprising HBsAg.

Accordingly, in a further aspect of the invention there is provided a stable and effective combined vaccine composition directed to the prevention of more than two diseases, comprising HBsAg and at least two other antigens.

In regards to a choice of adjuvant, excellent results are obtained when the HBsAg is adsorbed on AP and at least one of the antigens other than HBsAg is adsorbed to AH. Other suitable adjuvants may, however, be used. For example, one or all of the antigens other than HBsAg may be adsorbed to AP.

Preferred stable combination vaccines according to the invention are

Diphtheria-Tetanus-Pertussis-Hepatitis B (DTP-HB);

Diphtheria-Tetanus-Hepatitis B (DT-HB); or

DTP-IPV (inactivated polio vaccine)-Hepatitis B.

It will be appreciated that for a vaccine containing a Hib component the Hib antigen may be used extemporaneously by formulating the vaccine just prior to administration. In this way the following combined vaccine compositions within the scope of the invention may, for example, be prepared:

Hib-Hepatitis B;

DTP-Hib-Hepatitis B; or

IPV-DTP-Hib-Hepatitis B.

More specifically, particular vaccines within the scope of the invention are:

Diphtheria-Tetanus-Pertussis (DTP adsorbed on AH or AP)-Hepatitis B (HBsAg adsorbed on AP); and Diphtheria-Tetanus (DT adsorbed on AP or AH)-Hepatitis B (HBsAg adsorbed on AP).

By 'stable' as used herein to describe a vaccine according to the invention is meant a vaccine which can be kept a 37° C. for one week without any substantial loss of immunogenicity of the HBsAg component. For example, the titer (GMT) of Hepatitis B antibodies (AUSAB™, Abbott) is not statistically different from that obtained for the non-incubated vaccine using a non-parametric test (Robust). For example, $P \leq 0.1$. Preferably $P \leq 0.01$.

By 'effective' as used herein is meant a vaccine composition, characterized in that the immunogenicity of the HBsAg in the combined vaccine is such that a geometric mean titre of at least 200 mIU/ml, preferably 300 mIU/ml or greater, is found in human infants one month after the third dose of the vaccine when the vaccine is administered at one month intervals in an appropriate vaccination schedule. The Hepatitis B antibody titer is measured by the AUSAB™ assay (Abbott) using a WHO reference and expressed in mIU/mi. A titer of 10 mIU/ml is considered protective.

In a further aspect the invention provides a multivalent vaccine composition comprising HBsAg and a stabilizing adjuvant selected such that the vaccine can be kept at 37° C. for one week without any substantial loss in immunogenicity of the HBsAg component. Preferably the multivalent vaccine composition is further characterized by giving rise to a geometric mean titre of at least 200 mIU/ml (one month post third dose), preferably 300 mIU/ml or greater, in human infants when the vaccine is administered at one month intervals in an appropriate vaccination schedule.

As used herein the term 'appropriate vaccination schedule' means a schedule known to those of skill in the art for administering a course of doses of a vaccine, especially for pediatric doses. A schedule of 3, 4 and 5 months may, for example, be used. This is particularly appropriate for example for DTP-HBsAg containing vaccines according to the invention.

In one aspect the HBsAg can be adsorbed to an aluminium salt other than aluminium hydroxide. Preferably it is adsorbed to AP. The other antigens in the multivalent vaccine formulation may be adsorbed to AP or AH (or both) and are advantageously adsorbed to AH as shown in the examples hereinbelow.

Preferably the vaccine formulation according to the invention also comprises a pertussis vaccine.

The pertussis component is suitably a whole cell pertussis vaccine or an acellular pertussis vaccine containing partially or highly purified antigens.

The above combinations may optionally include a component which is protective against Hepatitis A, i.e. an HAV antigen.

Preferably the Hepatitis B combination vaccine is a pediatric vaccine.

The preparation of the antigens and adsorption procedure with the adjuvants are well known in the art, see for example, as given below.

The preparation of Hepatitis B surface antigen (HBsAg) is well documented. See, for example, Harford et al.(1983) in *Develop. Biol. Standard* 54, page 125, Gregg et al. (1987) in *Biotechnology* 5, page 479, EP A-0 226 846, EP A-0 299 108 and references disclosed therein.

As used herein the expression 'Hepatitis B surface antigen' or 'HBsAg' includes any HBsAg antigen or fragment thereof displaying the antigenicity of HBV surface antigen. It will be understood that in addition to the 226 amino acid sequence of the HBsAg S antigen (see Tiollais et al, *Nature* 317, 489 (1985) and references therein) HBsAg as herein described may, if desired, contain all or part of a pre-S sequence as described in the above references and in EP-A-0 278 940. In particular the HBsAg may comprise a polypeptide comprising an amino acid sequence comprising residues 12–52 followed by residues 133–145 followed by residues 175–400 of the L-protein of HBsAg relative to the open reading frame on a Hepatitis B virus of ad serotype (this polypeptide is referred to as L*; see EP 0 414 374 and is hereby incorporated by reference). HBsAg within the scope of the invention may also include the preS1–preS2-S polypeptide described in EP 0 198 474 (Endotronics) or analogues thereof such as those described in EP 0 304 578 (Mc Cormick and Jones). HBsAg as herein described can also refer to mutants, for example the 'escape mutant' described in WO 91/14703 or European Patent Application Publication Number 0 511 855 A1, especially HBsAg wherein the amino acid substitution at position 145 is to arginine from glycine.

Normally the HBsAg will be in particle form. The particles may comprise for example S protein alone or may be composite particles, for example (L*,S) where L* is as defined above and S denotes the S-protein of HBsAg. The said particle is advantageously in the form in which it is expressed in yeast.

Suitable antigens for use in vaccines according to the invention are already commercially available and details may be obtained from the World Health Organization. For example, the IPV component may be the Salk inactivated polio vaccine. The pertussis vaccine may comprise a whole cell product, an acellular product or a recombinantly produced product. In particular, the pertussis component can be PT (pertussis toxins) or subfractions thereof, FHA (filamentous haemagglutinin antigen), agglutinogens (fimbrial) and outer membrane proteins, including the 69kDa protein (pertactin, non fimbrial agglutinogen). See, for example, Robinson, A., Irons, L. I. & Ashworth, A. E., *Vaccines*, 3, 1985, 11–22; and Brennan, H. J., Li, S. M., Cowell, J. L., Bishen, M. E., Steven, A. C. Novotny., P, Manclarck, C. R., *Infection and Immunity*, 5, 1988, 3189–3195.

The component affording protection against Hepatitis A is preferably the product known as 'Havrix'™ (SmithKline Beecham Biologicals) which is a killed attenuated vaccine derived from the HM-175 strain of HAV [see, 'Inactivated Candidate Vaccines for Hepatitis A' by F. E. Andre, A. Hepburn and E. D'Hondt (1980), *Prog. Med. Virol.* Vol 37, pages 72–95 and the product monograph 'Havrix' published by SmithKline Beecham Biologicals (1991).].

Flehmig et al (loc cit., pages 56–71) have reviewed the clinical aspects, virology, immunology and epidemiology of Hepatitis A and discussed approaches to the development of vaccines against this common viral infection.

As used herein the expression 'HAV antigen' refers to any antigen capable of stimulating neutralizing antibody to HAV in humans. The HAV antigen preferably comprises inactivated attenuated virus particles or may be, for example, an HAV capsid or HAV viral protein, which may conveniently be obtained by recombinant DNA technology.

Vaccine preparation is generally described in *New Trends and Developments in Vaccines* (1978), edited by Voller et al., University Park Press, Baltimore, Md. U.S.A.

The amount of antigen in each vaccine dose is selected as an amount which induces an immunoprotective response without significant, adverse side effects in typical vaccinees. Such amount will vary depending on which specific immunogens are employed. Generally it is expected that each dose will comprise 1–1000 µg of total immunogen, preferably 2–100 µg, more preferably 1–40 µg, most preferably 1–5 µg. An optimal amount for a particular vaccine can be ascertained by standard studies involving observation of antibody titres and other responses in subjects. A primary vaccination course may include 2 or 3 doses of a vaccine, given one to two months apart, following the WHO recommendations for DTP immunization.

The invention thus provides a method of preventing hepatitis B and other infections in humans, especially infants, which method comprises treating a human subject in need thereof with an immunologically effective dose of a vaccine according to any aspect of the invention as hereinabove described.

In a further aspect of the invention there is provided a vaccine composition according to the invention for use in medicine.

In a further aspect of the invention there is provided the use of HBsAg for the manufacture of a combination vaccine according to the invention for the prophylaxis of Hepatitis B viral infections.

In a further aspect the invention provides the use of AP for the purpose of acting as a stabilizer for, and/or to maintain the efficacy of, HBsAg in a multivalent vaccine according to the invention.

Specifically the invention provides the use of aluminium phosphate for the purpose of preparing a stable combined vaccine comprising HBsAg and at least one other antiger, (preferably at least two other antigens) whereby the stability and/or immunogenicity of the HBsAg component is greater than in the corresponding combined vaccine in which the HBsAg component is adsorbed on AH.

More specifically the invention provides the use whereby the vaccine can be kept at 37° C. for 1 week (i.e., 7 days) without substantial loss of immunogenicity of the HBsAg.

Also provided is the use whereby the geometric meant titre (GMT) found one month after the third dose of a course of vaccinations given at one month intervals in an appropriate vaccination schedule to human infants is greater than 200, preferably greater than 300, mIU/ml.

In a further aspect of the present invention there is provided a method of manufacture of a combined (i.e., bivalent or multivalent) vaccine effective in preventing hepatitis B infection as illustrated in the examples hereinbelow.

In one preferred aspect the antigens other than HBsAg are all adsorbed on AH. A very effective DTPa-Hepatitis B vaccine can, for example, be made in this way.

In general, the combined vaccine compositions according to any aspect of the invention can be prepared as follows. The required DT, DTPw, DTPa, HA or other components are adsorbed onto a suitable adjuvant, especially AH or AP; HBsAg is adsorbed onto a suitable stabilizing adjuvant, selected as hereinabove described, especially an aluminium salt other than AH. Preferably it is adsorbed onto AP. After allowing time for complete and stable adsorption of the respective components, the different components are combined under appropriate conditions.

It will be appreciated that certain components, for example the DT, DTPw and DTPa components can be combined separately before adding the adsorbed HBsAg component. Multivalent vaccines comprising HBsAg and other or additional antigens to those mentioned hereinabove may be prepared in a similar manner.

In a preferred aspect there is provided a method of preparing a combined vaccine composition according to the invention wherein the method comprises mixing aluminium phosphate—adsorbed HBsAg with one or more aluminium hydroxide or aluminium phosphate adsorbed antigens.

The following examples are not meant to be limiting, but are presented below to merely illustrate the invention.

EXAMPLES 1–5

Formulations

Particular formulations according to the present invention were prepared as described below.

Example 1 HBsAg Adsorption on $AlPO_4$ as Concentrate for Formulation of Combined Vaccines.

A suspension of aluminium phosphate containing 0.03 to 0.3 g, preferably 0.1 to 0.2 g, of aluminium (as aluminium phosphate) in isotonic saline is mixed with a HBsAg concentrate containing 10 mg HBsAg protein in a final volume of 10 to 100 ml. After adjusting the pH to 5–6.5, preferbly 5.2–6.0, the mixture is left 10–24 hrs, preferably 16 to 20 hrs, at room temperature with stirring. Antiseptic is then optionally added (i.e., merthiolate, 1:20,000 to 1:10,000 or 2-phenoxyethanol, 3 to 6 mg/ml).

Example 2 Formulation of Combined Diphtheria-Tetanus-Hepatitis B Vaccine.

A concentrate containing 25,000 Lf* of diphtheria (D) toxoid and 10,000 Lf of tetanus (T) toxoid adsorbed to 0.35 g Al (as aluminium hydroxide or aluminium phosphate) is prepared in a final volume of 0.15 l of isotonic saline and adjusted to between pH 6 and 7, as specified by WHO for DT and DTP vaccines. This concentrate is combined with 0.05 l of the Hepatitis B concentrate of example 1.

This mixture is brought to a final volume of 0.5 l with isotonic saline. Antiseptic media (c.c. merthiolate 1:20,000 to 0:10,000 or 2-phenoxyethanol, 3 to 6 mg/ml) can be optionally added. The final pH is between 6 and 7, as specified by WHO for DT and DTP vaccines.

One 0.5 mnl dose of this bulk vaccine contains, as active ingredients:

*LF is a flocculation unit used to quantify an antigen, e.g., diptheria toxoid, in a flocculation assay using antibodies raised to the antigen, e.g., anti-diptheria toxoid antibodies.

D toxoid: 25 Lf

T toxoid: 10 Lf

HBsAg: 10 µg protein

The procedure can be optionally amended to use higher or lower quantities of the active ingredients.

Example 3 Formulation of Combined Diphtheria-Tetanus-Pertussis (whole cell vaccine)-Hepatitis B Vaccine A concentrate ex Behringwerke (Marburg, Germany) containing 7,500 Lf of diphtheria toxoid, 3,250 Lf of Tetanus toxoid and 15,000 opacity units* of *B. perrussis* antigen adsorbed to 0.45 mg Al (as alumninium hydroxide and aluminium phosphate) is prepared in a final volume of 0.4 l of isotonic saline and adjusted to pH 6–7, as specified by WHO for DTP vaccines. This concentrate is combined with 0.05 l of Hepatitis B concentrate of example 1.

This mixture is brought to a final volume of 0.5 l with isotonic saline. Antiseptic media (c.c. merthiolate 1:20,000 to 0:10,000 or 2-phenoxyethanol, 3 to 6 mg/ml) can be optionally added. The final pH is between 6 and 7, as specified by WHO for DT and DTP vaccines.

One 0.5 ml dose of this bulk vaccine contains, as active ingredients:

D toxoid: 7.5 Lf

T toxoid: 3.25 Lf

Pw antigen: 15 OU

HBsAg: 10 μg protein.

*OU relates to the concentration of a suspension, e.g., Pw.

The procedure can be optionally amended to use higher or lower quantities of the active ingredients.

Example 4 Formulation of Diphtheria-Tetanus-Pertussis (acellular component) Vaccine.

A concentrate containing 25,000 Lf of diphtheria toxoid and 10,000 Lf of tetanus toxoid adsorbed to 0.35 g Al (as aluminium hydroxide or phosphate gel) is prepared in a final volume of 0.15 l of isotonic saline and adjusted to between pH 6 and 7, as specified by WHO for DTP vaccines. 25 mg of inactivated pertussis toxin (PT), 25 mg of filamentous hemagglutinin (FRA) and optionally 8 mg of 69kDa outer membrane protein (pertactin), each combined with 0.05 g Al (as aluminium hydroxide or aluminium phosphate) are added. The *B. pertussis* antigens PT, FHA and pertactin can be prepared as described by methods known in the art, for example European patent application 427 462, PCT application WO 91/12020 or by other procedures giving physiologically acceptable and potent *B. pertussis* antigens.

This mixture is brought to a final volume of 0.5 l with isotonic saline. Antiseptic media (c.c. merthiolate 1:20,000 to 0:10,000 or 2-phenoxyethanol, 3 to 6 mg/ml) can be optionally added. The final pH is between 6 and 7, as specified by WHO for DT and DTP vaccines.

One 0.5 ml dose of this bulk vaccine contains, as active ingredients:

D toxoid: 25 Lf

T toxoid: 10 Lf

PT toxoid: 25 μg

FHA:* 25 μg

69kDa OMP:* 8 μg (optional)

*formalin-treated

The procedure can be optionally amended to use higher or lower quantities of the active ingredients.

Example 5 Formulation of Combined Diphtheria-Tetanus-Pertussis (acellular component)-Hepatitis B Vaccine The procedure of example 4 is applied, with the exception that an additional 50 ml of HBsAg adsorbed concentrate as prepared in example 1 is added to the final mixture.

The resulting mixture is brought to a final volume of 0.5 l with isotonic saline. Antiseptic media (c.c. merthiolate 1:20,000 to 0:10,000 or 2-phenoxyethanol, 3 to 6 mg/ml) can be optionally added. The final pH is between 6 and 7, as specified by WHO for DT and DTP vaccines.

One 0.5 ml dose of this bulk vaccine contains, as active ingredients:

D toxoid: 25 Lf

T toxoid: 10 Lf

PTd toxoid: 25 μg

FHA toxoid: 25 μg

69kDaOMP: 8 μg (optional).

The procedure can be optionally amended to use higher or lower quantities of the active ingredients.

EXAMPLES 6–10

Animal and Human Studies

Example 6 Formulation of Combined Hepatitis A-Hepatitis B Vaccines

An inactivated Hepatitis A virus concentrate (460,000 Elisa units—determnined by a standard binding assay), adsorbed to 0.02 to 0.2 g, preferably 0.04–0.1 g aluminium (as aluminium hydroxide) in a final volume of about 125 ml was combined to 50 ml of concentrate containing 10 mg HBsAg adsorbed to aluminium phosphate as described in example 1.

The resulting mixture was supplemented with isotonic saline and an amino acid concentrate (Travasol™, Baxter-Travenol Inc) to obtain a final volume of 0.5 l containing 1.5 g amino acids. The resulting pH was between 6 and 7.

A 1 ml dose of this bulk vaccine contains, as active ingredients:

Hepatitis A virus antigen: 800 Elisa units

HBsAg: 20 μg protein

The procedure can be optionally amended to use higher or lower quantities of the active ingredients.

Results:

Clinical Studies Comparing Aluminium Hydroxide (AH) and Aluminium Phosphate (AP) Adsorbed HBsAg (Monovalent vaccine)

Initially seronegative healthy adult volunteers were immunized with 3 doses of 20 μg HBsAg protein given at one month intervals. Antibody levels were determined in sera obtained one month post 2 and 3 doses using the AUSAB™ (Abbott) test. Responses were defined as subjects with titres significantly above background. Titres were expressed in mIU/ml. % responders represent the seroconversion rate.

Results are expressed as Geometric Mean Titres (GMT) in mIU/ml.

| HBsAg Lot | Adjuvant | N.Subj. | Post 2, month 2 | | Post 3, month 3 | |
| --- | --- | --- | --- | --- | --- | --- |
| | | | GMT | % responders | GMT | % responders |
| 100 | AH | 43 | 32 | 86 | 141 | 100 |
| 101 | AH | 45 | 26 | 93 | 198 | 98 |
| 102 | AH | 46 | 30 | 84 | 147 | 93 |
| 105/P | AP | 7 | 43 | 83 | 380 | 100 |
| 102 | AH | 51 | 14 | 82 | 126 | 98 |
| 103 | AH | 50 | 15 | 83 | 110 | 98 |
| 102 | AH | 54 | 17 | 83 | 133 | 96 |
| 104/P | AP | 54 | 18 | 96 | 270 | 98 |
| 105/P | AP | 51 | 14 | 90 | 156 | 96 |

Example 7

Mouse Immunogenicity Tests and Results of Accelerated Stability Tests for Combination Vaccines Comprising HBsAg with Aluminium Hydroxide (AH) or Aluminium Phosphate (AP) as Adjuvant Groups of 10 OF1 mice (IFFA-CREDO, France) were immunized subcutaneously with 2 doses of 2.5 μg HBsAg (single component or combined) at days 0 and 14. Blood was drawn off at day 21 and titrated for anti-HBsAg using the AUSAB™ (Abbott) test. Antibody titres were calculated in mIU/ml. The number of responding animals was defined as the number of those with antibody levels significantly above background values. The geometric mean titres was also calculated (GMT).

The results of DT-HB, DTPw-HB, DTPa-HB show that AP adsorbed HBsAg performed better than AH adsorbed HBsAg both in terms of number of responding animals and GMTs. The response to AP adsorbed HBsAg in the combination was comparable to that obtained by monovalent HBsAg administration.

|  | 7 days, 4° C. | | 7 days, 37° C. | | 7 days, 45° C. | |
| --- | --- | --- | --- | --- | --- | --- |
| Vaccine | N.resp. | GMT | N.resp. | GMT | N.resp | GMT |
| Engerix B ™ (HB + AH) | 7/10 | 30 | 9/10 | 17 | 6/10 | 2.7 |
| Engerix B ™ (HB + AH) | 9/10 | 54 | 8/10 | 13 | 5/10 | 6 |
| HB (AH) | 9/10 | 45 | 10/10 | 55 | 9/10 | 32 |
| HB (AP) | 9/10 | 54 | 10/10 | 50 | 7/10 | 6.9 |
| DTPw(AH)HB(AH) | 4/10 | 1.4 | nd | nd | nd | nd |
| DTPw(AH)HB(AP) | 9/10 | 52 | 8/10 | 16 | 8/10 | 26 |
| DT(AH)HB(AH) | 6/10 | 1.7 | nd | nd | nd | nd |
| DT(AH)HB(AP) | 8/10 | 44 | 9/10 | 21 | 10/10 | 36 |
| DTPa(AH)HB(AH) | 5/10 | 1.7 | nd | nd | nd | nd |
| DTPa(AH)HB(AP) | 10/10 | 18 | 8/10 | 8 | 9/10 | 24 | nd: not tested

Example 8

Immunogenicity of HBsAg Combined to DTPw in Monkeys Results of Aluminium Hydroxide (AH) and Aluminium Phosphate (AP) Adsorbed Antigen

*Cercopithenus aethiops* monkeys received two injections of 10 μg HBsAg (alone or combined) at days 0 and 30. Sera were withdrawn at days 30 and 57 and titrated (AUSAB™, Abbott) for anti-HbsAg. Animals with antibody levels significantly above background (pre-vaccination sera) were considered responders. GMT were calculated in mIU/ml.

Results show AP adsorbed HBsAg performed better than AH adsorbed HBsAg. The response was comparable to that obtained by monovalent HBsAg administration.

|  | Post 1, day 30 | | Post 2, day 57 | |
| --- | --- | --- | --- | --- |
| Vaccine | N. resp. | GMT | N. resp. | GMT |
| Engerix B ™ (HB)(AH) | 4/5 | 10 | 5/5 | 666 |
| DTPw(AH)HB(AH) | 4/5 | 20 | 5/5 | 31 |
| DTPw(AH)HB(AP) | 5/5 | 12 | 5/5 | 414 |

Example 9

Clinical Studies with Combined DTPw Vaccines using HBsAg Adsorbed to Aluminium Hydroxide (AH) or Aluminium Phosphate (AP)

Subjects were immunised with 3 doses of 0.5 ml containing DTPw and 10 μg HBsAg protein given at the age of 3, 4 and 5 months. Bleeding was at 6 months and sera were titrated with the AUSAB™ test. Percentage responders (seroconversion) relates to subjects with antibody levels significantly above background (i.e., >1 mIU/ml). Percentage protection is the protection rate and corresponds to subjects with titres equal to or greater than 10 mIU/ml. GMT in mIU/ml.

Results for DTPw-HB show AP adsorbed HBsAg produced a satisfactory response as opposed to AH adsorbed HBsAg Seroconversion rates and GMT were comparable to data typically seen with monovalent HBsAg vaccine (Engerix B)™.

| Vaccine | N. subj. | Bleeding Time | % resp. | % prot. | GMT |
| --- | --- | --- | --- | --- | --- |
| DTPw(AH).HB(AH) | 32 | post 2 | nd | nd | nd |
|  |  | post 3 | 94 | 84 | 38.5 |
| DTPw(AH).HB(AP) | 29 | post 2 | 97 | 97 | 63 |
|  | 17 | post 3 | 100 | 100 | 469 |

Example 10

Immunogenicity and Stability of HBsAg Adsorbed to Aluminium Hydroxide (AH) or Aluminium Phosphate (AP) in a Hepatitis A-Hepatitis B Combined Vaccine Groups of 10 OF1 mice were immunised subcutaneously with 2 doses of 2.5 μg HBsAg (single component or combined) at days 0 and 14. Blood was drawn at day 21 and titrated for anti-HBsAg as in Example 7.

Results for immunogenicity and stability of HA-HB combined product showed AP adsorbed HBsAg produced higher antibody levels and a more stable form.

| Vaccine | Exposure | N. resp. | GMT |
| --- | --- | --- | --- |
| HA(AH).HB(AH) | 1 month, 4° C. | 9/10 | 41 |
|  | 1 month, 37° C. | 6/10 | 5.6 |
|  | 1 month, 45° C. | 5/10 | 6.4 |
| HA(AH).HB(AP) | 1 month, 4° C. | 10/10 | 80 |
|  | 1 month, 37° C. | 9/10 | 45 |
|  | 1 month, 45° C. | 8/10 | 18 |
| Engerix B ™ HB(AH) | 1 month, 4° C. | 8/10 | 58 |

Example 11: Further Clinical Results in Humans
1. Immunogenicity of DTPw-Hepatitis B Vaccines in Infants
Experiment A
Schedule: 3–4–5 Months. 10 μg HBsAg; DTPw ex Behringwerke (DT on AH; Pw on a mixture of AH and AP)

| Anti-Hbs titres | | | | |
| --- | --- | --- | --- | --- |
| HBsAg adjuvant | Time | N | GMT | SP (%) |
| Al Hydroxide | Post II (5 months) | 44 | 45 | 79.5 |
| Al Hydroxide | Post III (6 months) | 13 | 34 | 69.2 |
| Al Phosphate | Post II (5 months) | 32 | 80 | 97.0 |
| Al Phosphate | Post Ill (6 months) | 32 | 396 | 100 |

In this and other examples Post II means after the second dose, post III after the third dose. GMT is always measured one month after the injection time shown in the schedule. SP is the seroprotection rate.

| Anti-Diphtheria, Tetanus, B pertussis titres | | | | |
| --- | --- | --- | --- | --- |
| Post III results | N | GMT | % > 0.1 IU/ml | GMT Post/Pre |
| Anti-Diphtheria | 38 | 2.302 | 100 | 37.4 |
| Anti-Tetanus | 38 | 3.281 | 100 | 38.4 |
| Anti-B pertussis | 38 | 61 | — | 7.7 |

Experiment B
Schedule 2–4–6 Months (same vaccine as for Experiment A)

| Anti-HBs titres (interim results) | | | | |
| --- | --- | --- | --- | --- |
| HBsAg adjuvant | Time | N | GMT | SP (%) |
| Al Hydroxide | Month 7 | 22 | 284 | 90.5 |

-continued

Anti-HBs titres (interim results)

| HBsAg adjuvant | Time | N | GMT | SP (%) |
|---|---|---|---|---|
| Al Hydroxide | Month 7 | 17 | 193 | 94.4 |
| Al Phosphate | Month 7 | 23 | 1794 | 92.0 |

Experiment C
Schedule 3–4–5 (HBsAg=5 µg on Aluminium Phosphate; DTP ex Behringwerke as for Experiment A)

Anti-HBs titres

| Time | N | GMT | SP (%) |
|---|---|---|---|
| Post II | 21 | 94 | 90.5 |
| Post III | 18 | 311 | 100 |

Experiment D
Schedule 3–4–5 Months of Age (HBsAg=10 µg on Aluminium Phosphate; DTPw ex Behringwerke as for Experiment A)

Anti-HBs titres

| Time | N | GMT | SP (%) |
|---|---|---|---|
| Pre | 24 | 0 | 0 |
| Post II (month 5) | 13 | 259 | 92.3 |
| Post III (month 6) | 10 | 592 | 100.0 |

| Timing | N | GMT | SP (%) | GMT Post/Pre |
|---|---|---|---|---|
| Anti-diphtheria antibodies | | | | |
| Pre vaccination | 32 | 0.054 | 6.3 | 1.0 |
| Post II | 16 | 1.094 | 93.8 | 20.4 |
| Post III | 11 | 2.314 | 100.0 | 43.1 |
| Anti-tetanus antibodies | | | | |
| Pre vaccination | 32 | 0.083 | 34.4 | 1.0 |
| Post II | 16 | 3.146 | 100.0 | 37.9 |
| Post III | 11 | 7.989 | 100.0 | 96.4 |

| Timing | N | GMT | | GMT Post/Pre |
|---|---|---|---|---|
| Anti-B pertussis antibodies | | | | |
| Pre vaccination | 32 | 8 | | 1.0 |
| Post II | 16 | 20 | | 2.7 |
| Post III | 11 | 50 | | 6.6 |

2. Immunogenicity of DTPa-Hepatitis B Vaccines in Infants
Experiment A
HBsAg 10 µg on AP; DTP (acellular) on AH. Preliminary Results

| Timing | N | S+ | % | GMT |
|---|---|---|---|---|
| Group 1 (DTPa - Engerix B combination) | | | | |
| Pre vaccination | 19 | 0 | 0 | 0 |
| Post I | 19 | 4 | 21.1 | 24 |
| Post II | 19 | 18 | 94.7 | 146 |
| Post III | 19 | 19 | 100.0 | 345 |

-continued

| Timing | N | S+ | % | GMT |
|---|---|---|---|---|
| Group 2 (DTPa plus Engerix B; separate simultaneous injections) | | | | |
| Pre vaccination | 8 | 0 | 0 | 0 |
| Post I | 8 | 2 | 25.0 | 37 |
| Post II | 8 | 5 | 62.5 | 33 |
| Post III | 7 | 6 | 83.7 | 385 |

Key: N=number of subjects tested; S+=number of subjects seropositive at a given blood sampling time; %=seroconverion rate and GMT=geometric mean antibody titre of seroconverters

We claim:

1. A combined vaccine composition comprising Hepatitis B surface antigen (HBsAg) and a number (n) of other antigens against one or more of the following pathogens: diphtheria, tetanus, pertussis, polio, Haemophilus influenzae b, Hepatitis A, meningitis A, meningitis B, meningitis C, and otitis media, in combination with an adjuvant comprising one or more aluminum salts and in which the adjuvant used to adsorb the HBsAg is aluminum phosphate, with the proviso that when n is 1 the other antigen is not an antigen against hepatitis A.

2. The combined vaccine composition according to claim 1 in which the HBsAg is adsorbed to aluminium phosphate and in which at least one of the other antigens is adsorbed to aluminium phosphate.

3. The combined vaccine composition according to claim 1 in which the HBsAg is adsorbed to aluminium phosphate and at least one other antigen is adsorbed to aluminium hydroxide.

4. The combined vaccine composition according to claim 1 wherein n is 2, 3, 4, 5 or 6.

5. The vaccine composition according to claim 1 wherein n is greater than 1; the HBsAg is adsorbed to aluminium phosphate; and the antigen other than HBsAg is adsorbed to aluminium hydroxide or aluminium phosphate and is selected from the group consisting of an antigen for immunizing against diphtheria (D); tetanus (T); pertussis (P); Inactivated Polio (IPV); Haemophilus influenzae b (Hib) and Hepatitis A (HA).

6. A stable and effective combined vaccine composition directed to the prevention of more than two diseases comprising HBsAg and at least two other antigens against two or more of the following pathogens: diphtheria, tetanus, pertussis, polio, Haemophilus influenzae b, Hepatitis A, meningitis A, meningitis B, meningitis C, and otitis media, in which the HBsAg is adsorbed to aluminum phosphate.

7. The combined vaccine composition according to claim 6 in which at least one of the antigens other than HBsAg is adsorbed to aluminium hydroxide.

8. The combined vaccine composition according to claim 6 which is selected from the group consisting of Diphtheria-Tetanus-Pertussis (DTP)-Hepatitis B, Diphtheria-Tetanus (DT)-Hepatitis B and DTP-IPV (inactivated polio vaccine)-Hepatitis B.

9. The combined vaccine composition according to claim 6 in which the stability of the vaccine is such that the vaccine can be kept at 37° C. for 1 week without substantial loss of immunogenicity of the HBsAg component.

10. The vaccine composition according to claim 6 wherein the immunogenicity of the HBsAg in the combined vaccine is such that a geometric mean titer of 200 mIU/ml (one month post third dose) or greater is found in human infants when a course of the vaccine is given at one month intervals in an appropriate vaccination schedule.

11. The vaccine composition according to claim 6 comprising an antigen component which is protective against Hepatitis A.

12. The vaccine composition according to claim 6 which comprises a pertussis component.

13. The vaccine according to claim 6 which comprises a pertussis component and in which the pertussis component is a whole cell pertussis antigen or an acellular pertussis antigen.

14. The combined vaccine composition according to claim 6 further characterized in that it gives rise to a geometric mean titer of at least 200 mIU/ml (1 month post third dose) when a course of the vaccine is given to human infants at one month intervals in an appropriate vaccination schedule.

15. The combined vaccine composition according to claim 6 in which the adjuvant is selected from one or more aluminium salts with the proviso that the HBsAg component is not adsorbed on aluminium hydroxide.

16. The combined vaccine composition according to claim 6 which is Diphtheria-Tetanus-Pertussis (acellular)-HBsAg, in which the DT-acellular Pertussis is adsorbed on aluminum hydroxide and the HBsAg is adsorbed on aluminum phosphate.

17. The combined vaccine composition according to claim 6 which is Diphtheria-Tetanus-Pertussis (whole cell)-HBsAg, in which the DT-whole cell Pertussis is adsorbed on aluminum hydroxide and the HBsAg is adsorbed on aluminum phosphate.

18. A method of preparing a stable and effective vaccine composition wherein the method comprises admixing aluminium phosphate—adsorbed to HBsAg, with one or more antigens adsorbed to aluminium hydroxide or aluminium phosphate, with the proviso that when one antigen is used it is not an antigen providing immunity against Hepatitis A infection and recovering said stable and effective combination vaccine.

19. A method of preventing hepatitis B infections in humans, which method comprises treating human subjects in need thereof with an effective dose of the combined vaccine of claim 1.

20. A method of preventing hepatitis B infections in humans, which method comprises treating human subjects in need thereof with an effective dose of the combined vaccine of claim 6.

* * * * *